US012691170B2

(12) United States Patent
Suarez et al.

(10) Patent No.: US 12,691,170 B2
(45) Date of Patent: Jul. 28, 2026

(54) AVIAN INFLUENZA VACCINES AND METHODS OF MAKING SAME

(71) Applicant: The United States of America, as represented by The Secretary of Agriculture, Washington, DC (US)

(72) Inventors: David L. Suarez, Athens, GA (US); Mary J. Pantin Jackwood, Watkinsville, GA (US); Sungsu Youk, Athens, GA (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 619 days.

(21) Appl. No.: 18/187,934

(22) Filed: Mar. 22, 2023

(65) Prior Publication Data

US 2023/0321215 A1     Oct. 12, 2023

Related U.S. Application Data

(60) Provisional application No. 63/328,911, filed on Apr. 8, 2022.

(51) Int. Cl.
| | |
|---|---|
| *A61K 39/145* | (2006.01) |
| *A61P 31/14* | (2006.01) |
| *C07K 14/005* | (2006.01) |
| *C12N 15/86* | (2006.01) |
| *A61K 39/00* | (2006.01) |

(52) U.S. Cl.
CPC ............ *A61K 39/145* (2013.01); *A61P 31/14* (2018.01); *C07K 14/005* (2013.01); *C12N 15/86* (2013.01); *A61K 2039/5254* (2013.01); *C12N 2760/16122* (2013.01); *C12N 2760/16134* (2013.01); *C12N 2760/16144* (2013.01); *C12N 2760/16152* (2013.01)

(58) Field of Classification Search
None
See application file for complete search history.

(56) References Cited

FOREIGN PATENT DOCUMENTS

| | | |
|---|---|---|
| WO | 2008/157203 A2 | 12/2008 |
| WO | 2020/264141 A1 | 12/2020 |

OTHER PUBLICATIONS

Harvey et al., Vaccine vol. 28, pp. 8008-8014 (Year: 2010).*
Nicolson et al., Vaccine vol. 23, Issue 22, pp. 2943-2952 (Year: 2005).*
Li et al. Virology 525, pp. 32-39 (Year: 2018).*
GeneBank access No. PV124886 (Year: 2025).*
GenEmbl access No. OQ550442 (Year: 2025).*
De Araújo et al. Emerging Infectious Diseases. Mar. 2024; 30 (3): 619) (Year: 2025).*
Hu et al. Computational Molecular Bioscience, 2013; 3: 32-37 (Year: 2013).*
R. Harvey, et al., 'Improved haemagglutinin antigen content in H5N1 candidate vaccine viruses with chimeric haemagglutinin molecules,' 2010, Vaccine 28: 8008-8014.
A. Johnson, et al., 'Identification of influenza A/PR/8/34 donor viruses imparting high hemagglutinin yields to candidate vaccine viruses in eggs,' 2015, PLoS ONE 10(6): e0128982.
J.-W. Jang, et al., 'Optimized clade 2.3.2.1c H5N1 recombinant-vaccine strains against highly pathogenic avian influenza,' 2017, J. Vet. Sci. 18(S1): 299-306.
L. Zhao, et al., 'New insights into the nonconserved noncoding region of the subtype-determinant hemagglutinin and neuraminidase segments of influenza A viruses,' 2014, J. Virol. 88 (19): 11493-11503.
International Search Report on PCT/US2023/064819 issued Jul. 7, 2023.
Written Opinion of the International Searching Authority on PCT/US2023/064819 issued Jul. 7, 2023.

* cited by examiner

Primary Examiner — Shanon A. Foley
Assistant Examiner — Myron G Hill
(74) Attorney, Agent, or Firm — John Fado; Maria Restrepo-Hartwig

(57) ABSTRACT

The disclosure relates to avian influenza vaccines produced through reverse genetics to protect from A/Turkey/Indiana/22-like virus, methods for producing such vaccines, and method for using such vaccines to protect poultry. The disclosure also relates to methods of producing influenza viruses comprising chimeric polynucleotides having an HA non-coding sequence from an apathogenic high growth influenza virus and a polynucleotide encoding an HA protein from a highly pathogenic avian influenza virus or variant thereof, and/or having a chimeric polynucleotide having an NA non-coding sequence from an apathogenic high growth influenza virus and a polynucleotide encoding an NA protein from a highly pathogenic avian influenza virus or variant thereof.

13 Claims, 2 Drawing Sheets

Specification includes a Sequence Listing.

AVIAN INFLUENZA VACCINES AND METHODS OF MAKING SAME

CROSS-REFERENCE TO RELATED APPLICATIONS

This application claims the benefit of U.S. Provisional Application No. 63/328,911 filed Apr. 8, 2022. The content of this provisional patent application is hereby expressly incorporated by reference in its entirety.

SEQUENCE LISTING

The instant application contains a Sequence Listing XML required by 37 C.F.R. § 1.831(a) which has been submitted in XML file format via the USPTO patent electronic filing system, and is hereby incorporated by reference in its entirety. The XML file was created on Mar. 22, 2023, is named Sequence Listing CONVERSION-0056.22.xml, and has 9,982 bytes.

FIELD OF THE INVENTION

The disclosure relates to avian influenza viruses produced through reverse genetics, and used as vaccines to protect from highly pathogenic avian influenza (HPAI), methods for producing such viruses, and methods for using such vaccines to protect poultry.

BACKGROUND OF THE INVENTION

Avian influenza, most commonly known as "bird flu" presents with devastating consequences for the poultry industry, farmers' livelihoods, international trade, and the health of wild birds. To contain the spread of avian influenza, it is often the policy to cull all poultry, whether infected or healthy in places where outbreaks occur. This represents heavy economic losses and a long-lasting impact on farmers' livelihoods. Avian influenza is also a major concern for public health. Whenever avian influenza viruses circulate in poultry, sporadic cases of avian influenza are sometimes identified in humans.

As of Mar. 23, 2022, the US Animal and Plant Health Inspection Service (APHIS) reported detection of HPAI-infected wild birds in South Dakota, Nebraska, Kansas, Iowa, Missouri, Illinois, Indiana, Kentucky, Tennessee, Alabama, Florida, Georgia, Ohio, South Carolina, North Carolina, Virginia, Maryland, Delaware, New Jersey, New York, Connecticut, Massachusetts, New Hampshire, and Maine. All confirmed infected birds were positive for the Eurasian H5N1 virus. Wild birds are capable of transmitting avian influenza to domestic poultry. Wild birds can be infected with the virus and may show no signs of illness. Wild birds have spread virus to domestic poultry, including numerous backyard poultry flocks and commercial turkey, layer, and broiler operations in multiple states. To date, over 20 million poultry have died or were euthanized to control the spread of the disease.

Influenza A viruses are genetically diverse pathogens that can infect various hosts including birds, swine, and humans. Vaccines and vaccination have emerged during the past three decades as essential tools in influenza control. Their use in poultry can increase resistance to infection, prevent illness and death, reduce virus replication and shed, and reduce virus transmission to birds and mammals, including humans.

Low pathogenicity avian influenza (LPAI) viruses typically cause little or no clinical signs in infected poultry. The LPAI virus is excreted through infected birds' feces and respiratory secretions. It spreads primarily through direct contact between healthy and infected birds. It can also be spread through indirect contact with contaminated equipment and materials. LPAI virus strains occur naturally in wild migratory waterfowl and shorebirds without causing illness. A highly pathogenic avian influenza virus (HPAI) is a serious disease and requires rapid response because it is highly contagious and deadly. It infects domestic poultry, such as chickens, turkeys, pheasants, quail, ducks, geese, and wild birds, particularly waterfowl. HPAI spreads from bird to bird by direct contact or through contact with contaminated water. manure, equipment, vehicles, crates, and the clothing or shoes of people who have come in contact with the virus.

DIVA stands for Differentiating Infected from Vaccinated Animals. For Avian influenza, this can be achieved by using a vaccine based on a different strain (e.g. H5N2) than the current field strain (e.g. H5N1) and using a serological test that can differentiate between vaccine-induced antibodies (e.g. against N2) and antibodies against the field virus (N1).

Novel influenza virus strains evolve readily and can spread amongst various species, thereby necessitating the continuous production of new vaccines. Because of the continual emergence or re-emergence of different influenza strains, new influenza vaccines are continually desired. Such vaccines typically are created using antigenic moieties of the newly emergent virus strains, thus, polypeptides and polynucleotides of novel, newly emergent, or newly re-emergent virus strains (especially sequences of antigenic genes) are highly desirable.

SUMMARY OF THE INVENTION

Provided herein are influenza vaccine viruses produced by reverse genetics, that provide protection against the current H5N1 field strain, and/or that provide DIVA (differentiating vaccinated from infected animals) capabilities.

The disclosure relates to avian influenza viruses produced through reverse genetics and used as vaccines to protect from highly pathogenic avian influenza (HPAI), methods for producing such viruses, and methods for using such vaccines to protect poultry.

In an embodiment, the disclosure relates to a chimeric polynucleotide comprising an apathogenic high growth influenza virus hemagglutinin (HA) non-coding sequence and a polynucleotide encoding HA protein from a highly pathogenic avian influenza virus or variant thereof, and/or an apathogenic high growth influenza virus neuraminidase (NA) non-coding sequence and a polynucleotide encoding an NA protein from a highly pathogenic avian influenza virus or variant thereof. In some embodiments of the disclosure, the polynucleotide encoding a variant of the HA protein has at least about 80% identity to the A/PuertoRico/8/34 (PR8) HA NA protein. In some embodiments of the disclosure the NA protein is an N1, N2, N3, N4, N5, N6, N7, N8, or N9 or a variant thereof. In some embodiments of the disclosure, the polynucleotide encoding a variant of the NA protein has at least about 80% identity to the N1, N2, N3, N4, N5, N6, N7, N8, or N9 protein. In some embodiments of the disclosure, the apathogenic high growth influenza virus is PR8.

In an embodiment, the disclosure relates to a rescued influenza virus comprising polynucleotides encoding PR8 M1/M2, NP, PB1, PA, PB2, and NS1/NS2, a A/turkey/Indiana/22-003707-003/2022 HA, and at least one N1, N2, N3, N4, N5, N6, N7, N8, or N9 NA.

In an embodiment, the disclosure relates to a method of producing an influenza virus, the method comprising introducing into a population of host cells a plurality of vectors comprising polynucleotides corresponding to at least six internal segments of PR8, at least one polynucleotide encoding A/turkey/Indiana/22-003707-003/2022 HA, and at least one polynucleotide encoding one of N1, N2, N3, N4, N5, N6, N7, N8, or N9, culturing the population of host cells at a temperature that is less or equal to 35° C., and recovering the virus.

BRIEF DESCRIPTION OF THE SEQUENCE LISTING

Figure 1:
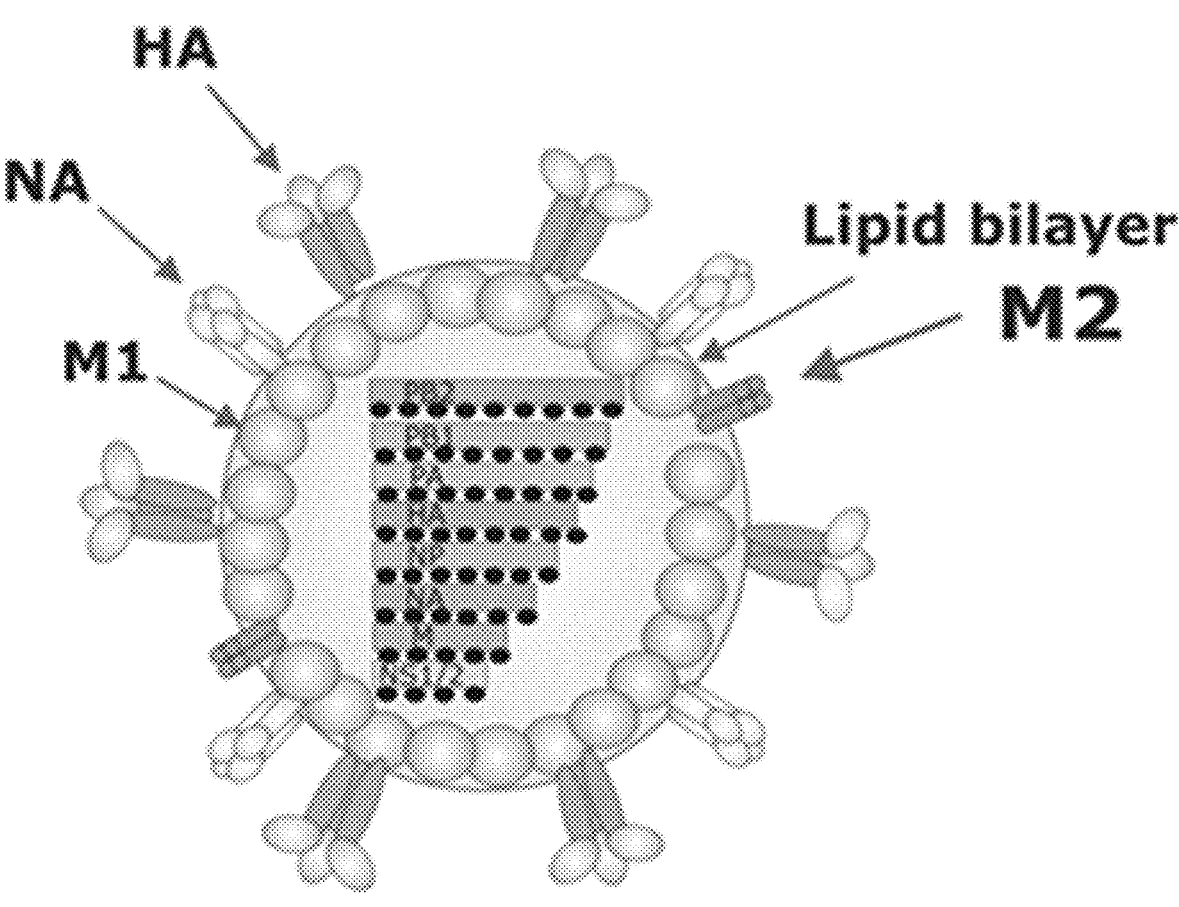
FIG. 1 depicts an influenza A virus schematic showing the virion shape, the lipid bilayer, the location of the membrane-bound proteins HA, NA, M1, and M2; and the genome segments PB2, PB1, PA, HA, NP, NA, M, and NS inside the virion.
Figure 2:
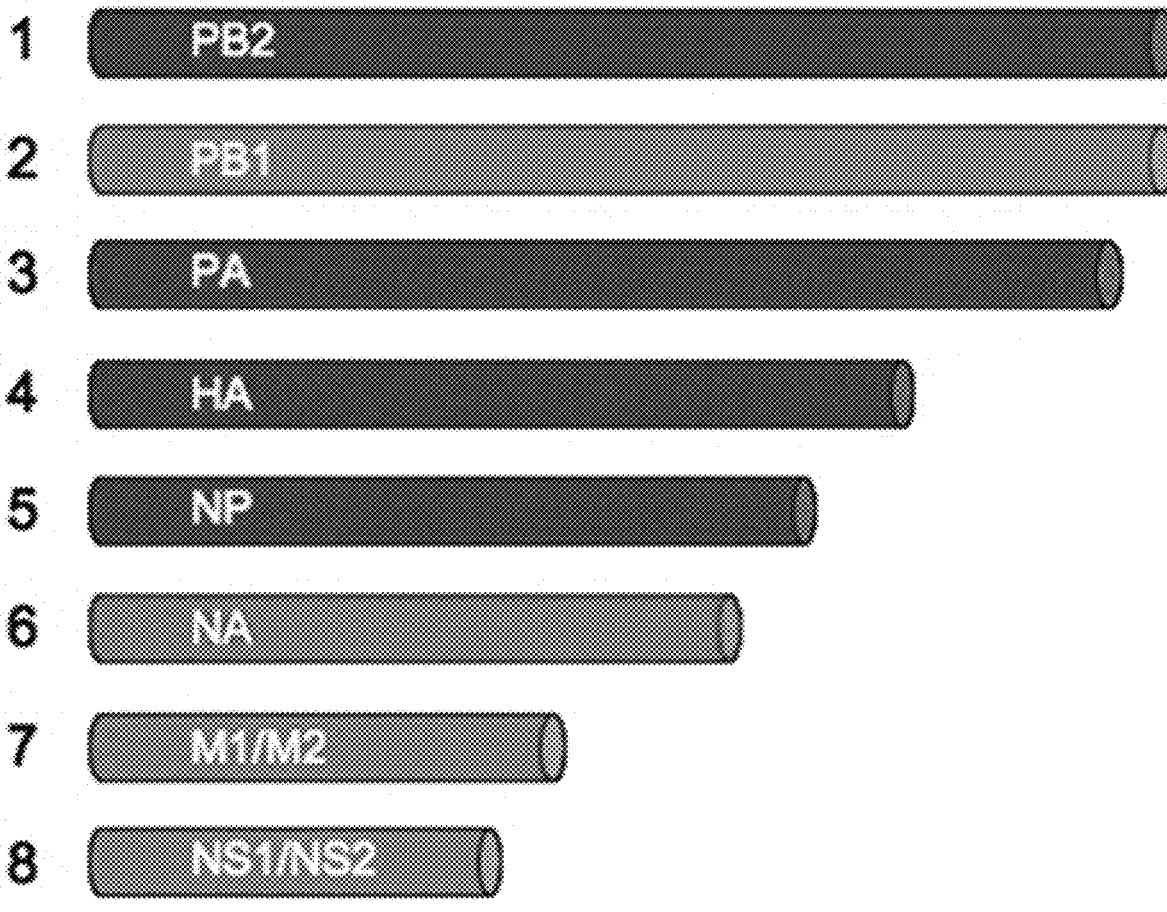
FIG. 2 depicts the eight gene segments present in the influenza A virion. Gene segment 1: PB2; gene segment 2: PB1; gene segment 3: PA; gene segment 4: HA; gene segment 5: NP; gene segment 6: NA; gene segment 7: MA; and gene segment 8: NS.

The nucleotide sequences disclosed in the specification are listed in Table 1, below.

| Sequence Identifier | Type | Description |
|---|---|---|
| SEQ ID NO: 1 | amino acid | A/turkey/Indiana/22-003707-003/2022 original HA cleavage site |
| SEQ ID NO: 2 | amino acid | Modified low pathogenic HA cleavage site |
| SEQ ID NO: 3 | DNA | A/turkey/Indiana/22-003707-003/2022 HA (H5) |
| SEQ ID NO: 4 | DNA | A/turkey/Indiana/22-003707-003/2022 NA (N1) |
| SEQ ID NO: 5 | DNA | A/Blue Winged Teal/Wyoming/AH0099021/2016 (N9) |

DETAILED DESCRIPTION

The disclosure relates to avian influenza vaccines to protect from HPAI produced through reverse genetics, kits comprising such vaccines, and method for using such vaccines to protect poultry.

As used herein, the term "about" is defined as plus or minus ten percent of a recited value. For example, about 1.0 g means 0.9 g to 1.1 g.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicates otherwise.

As used herein, the singular forms "a," "an," and "the" designate both the singular and the plural, unless the context clearly indicates otherwise.

The term "about" is intended to refer to ranges substantially within the quoted range while not departing from the scope of the disclosure. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the recited value.

The terms "individual," "subject," and "animal", are used interchangeably herein, and refer to vertebrates that support a negative strand RNA virus infection, specifically influenza A virus infection.

Exemplary subjects may include vertebrates of importance to humans due to being endangered, being of economic importance such as those raised on farms for consumption by humans, and/or being of social importance such as animals kept as pets or in zoos. The methods and compositions of the present disclosure are particularly useful for warm-blooded vertebrates including, but not limited to, birds, Canidae, Cetacea, Felidae, Mustelidae, Rodentia, Equidae, Bovidae, Suidae, and Primates. In some embodiments the vertebrates are birds such as water fowl, chickens, or turkeys. In some embodiments the vertebrates are mammals such as pigs, horses, whales, dolphins, or humans. In some embodiments the vertebrates are humans. In some embodiments the vertebrates are chickens.

As used herein, the terms "isolated," and "purified" refer to material that is substantially or essentially free from components that normally accompany the referenced material in its native state.

As used herein, "substantially free" means below the level of detection for a particular agent, using standard detection methods for that agent, such as unwanted nucleic acids, proteins, cells, viruses, infectious agents, etc.

As used herein, an "amino acid sequence" is a character string representing a polymer of amino acid residues such as a protein, a polypeptide, or a polymer.

The terms "nucleic acid" and "polynucleotide" are used interchangeably herein and refer to single-stranded or double-stranded deoxyribonucleotide or ribonucleotide polymers, chimeras or analogues thereof.

As used herein, the terms "polynucleotide sequence" and "nucleic acid sequence" are used interchangeably and refer to a character string representing the polynucleotide or nucleic acid. Unless otherwise indicated, a particular nucleic acid sequence of this disclosure optionally encompasses complementary sequences in addition to the sequence explicitly indicated. From any specified polynucleotide sequence, either the given nucleic acid or the complementary polynucleotide sequence (e.g., the complementary nucleic acid) can be determined.

The term "gene" is used herein broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one that regulates transcription in a specific tissue type or cell type, or types.

An "open reading frame" or "ORF" is a possible translational reading frame of DNA or RNA (e.g., of a gene), which is capable of being translated into a polypeptide. That is, the reading frame is not interrupted by stop codons.

However, it should be noted that the term ORF does not necessarily indicate that the polynucleotide is, in fact, translated into a polypeptide.

As used herein, "Expression of a gene" or "expression of a nucleic acid" mean transcription of DNA into RNA (optionally including modification of the RNA, e.g., splicing), translation of RNA into a polypeptide (possibly including subsequent modification of the polypeptide, e.g., post-translational modification), or both transcription and translation, as indicated by the context.

The term "vector" refers herein to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present disclosure are plasmids.

An "expression vector" is a vector, such as a plasmid that is capable of promoting expression, as well as replication of a nucleic acid incorporated therein. Typically, the nucleic acid to be expressed is "operably linked" to a promoter and/or an enhancer, and is subject to transcription regulatory control by the promoter and/or the enhancer.

The term "polypeptide" is used herein to refer to a polymer comprising two or more amino acid residues (e.g., a peptide or a protein). The polypeptide can optionally comprise modifications such as glycosylation or the like. The amino acid residues of the polypeptide can be natural or non-natural and can be unsubstituted, unmodified, substituted, or modified.

As used herein, the term "DIVA" stands for Differentiating Infected from Vaccinated Animals. For Avian influenza, this can be achieved by using a vaccine based on a different strain (e.g., H5N2) than the current field strain (e.g., H5N1), and using a serological test that can differentiate between vaccine-induced antibodies (e.g., against N2) and antibodies against the field virus (N1). Because unvaccinated animals will die and not develop a serologic response, the DIVA vaccine of the disclosure may be used to differentiate vaccinated and infected animals from vaccinated animals.

As used herein, a "recombinant virus" is one which has been manipulated in vitro, e.g., using recombinant nucleic acid techniques to introduce changes to the viral genome, or a virus that is artificially generated.

As used herein, the terms "recombinant nucleic acid," "recombinant segment," and "recombinant polynucleotide" are used interchangeably and refer to a nucleic acid that has been altered in vitro. The sequence of a recombinant polynucleotide is not naturally occurring, or does not correspond to naturally occurring sequences, or that are not positioned as they would be positioned in the native genome.

By "pharmaceutical composition" is meant a composition that contains a recombinant mutant influenza gene segment of the disclosure, or a recombinant influenza virus of the disclosure, and that is suitable for administration to a subject. The pharmaceutical composition is suitable to prevent, treat, reduce, or ameliorate one or more influenza symptoms in the subject. For the purposes of this disclosure, pharmaceutical compositions include vaccines.

As used herein "diluent," "excipient," "carrier," and "adjuvant" are used interchangeably, and refer to a diluent, excipient, carrier, or adjuvant which is physiologically acceptable to the subject while retaining the therapeutic properties of the pharmaceutical composition with which it is administered. Physiologically acceptable diluents, excipients, carriers, or adjuvants and their formulations are known to one skilled in the art (see, e.g., U.S. Pat. No. 9,017,691; Chaudhari S. P., et al. 2012, *Pharmaceutical Excipients: A Review*," IJAPBC Vol 1(1)). Reed S. G., et al. (2013, *"Key Roles of Adjuvants in Modern Medicines*," Nature Medicine 19(12): 1597-1608) review adjuvants used in vaccines.

As used herein, the term "attenuated," as used in conjunction with a virus, refers to a virus having reduced virulence or pathogenicity as compared to a non-attenuated counterpart, yet is still viable or live. Typically, attenuation renders an infectious agent, such as a virus, less harmful or virulent to an infected subject compared to a non-attenuated virus.

The terms "inoculated" and "vaccinated" are used interchangeably herein and refer to the act of introducing an influenza virus vaccine of the disclosure in birds.

The Orthomyxoviruses are a family of RNA viruses that includes seven genera: Influenza virus A, Influenza virus B, Influenza virus C, Influenza virus D, Isavirus, Thogotovirus, and Quaranjavirus. Influenza A virus is one of the world's major uncontrolled pathogens, causing seasonal epidemics as well as global pandemics. Influenza A viruses can infect various vertebrate hosts including birds and mammals. Influenza vertebrate hosts are birds, Canidae, Cetacea, Felidae, Mustelidae, Rodentia, Equidae, Bovidae, Suidae, and Primates. In some embodiments the vertebrates are birds such as water fowl, chickens, or turkeys. In some embodiments the vertebrates are mammals such as pigs, horses, whales, dolphins, or humans. In some embodiments the vertebrates are humans. In some embodiments the vertebrates are chickens, turkeys, dolphins, whales, swine, horses, or humans.

The genome of the Influenza A virus is negative-sense, single-stranded, segmented RNA. The Influenza A subtypes are named (HxNy) according to the type of hemagglutinin (H) and the type of neuraminidase (N) present in the virus. Up to date 18 different H antigens and 10 different N antigens are known.

The Influenza virus particle (also called a virion) is made of a viral envelope wrapped around a central core. The outer layer of the influenza virion is a lipid membrane taken from the host cell in which the virus multiplies. Inserted into the lipid membrane are the hemagglutinin (HA) protein, the neuraminidase (NA) protein, and the matrix-2 (M2) protein. Four M2 proteins form a proton-selective ion channel where the units are helices stabilized by two disulfide bonds. Beneath the lipid membrane is a layer of the matrix protein (M1) forming a shell. Within the interior of the virion are eight negative strand viral RNA segments consisting of RNA joined with the nucleoprotein (NP), and the three polymerase subunits (Polymerase Basic protein1 (PB1), Polymerase Basic protein 2 (PB2), and polymerase acidic protein (PA)). Non-Structural protein 1 (NS1) and Non-Structural protein 2 (NS2) are found in infected cells but are not packaged inside the virion.

The eight RNA segments of the influenza A viral genome are depicted in FIG. 1. Gene segment 1, also referred to as PB2 gene segment, encodes the cap-binding transcriptase PB2. Using alternative translation initiation sites, gene segment 2, also referred to as PB1 gene segment, encodes elongation-associated proteins PB1, PB1-F2, and PB1-N40.

By a ribosomal frameshift gene segment 3, also referred to as PA gene segment, encodes the polymerase acidic proteins PA and PA-X, and by using alternative translation sites and N-terminal truncation encodes PA-N155 and PA-N182. Gene segment 4, also referred to as HA gene segment, encodes the hemagglutinin protein HA. Gene segment 5, also referred to as NP gene segment, encodes the RNA binding nucleoprotein NP. Gene segment 6, also referred to as NA gene segment, encodes the neuraminidase protein NA. Gene segment 7, also referred to as the matrix gene, encodes two proteins M1 and M2. Gene segment 8, also referred to as non-structural gene, encodes the non-structural protein NS1, and by alternative RNA splicing it encodes NS3 and the nuclear export protein NS2/NEP.

Avian influenza is caused by influenza Type A virus (influenza A). Avian-origin influenza viruses are broadly categorized based on a combination of two groups of proteins on the surface of the influenza A virus: hemagglutinin or "H" proteins, of which there are 16 (H1-H16), and neuraminidase or "N" proteins, of which there are 9 (N1-N9). Many different combinations of "H" and "N" proteins are possible. Each combination is considered a different subtype, and related viruses within a subtype may be referred to as a lineage. Avian influenza viruses are classified as either "low pathogenic" or "highly pathogenic" based on their genetic features and the severity of the disease they cause in chickens. Most viruses are of low pathogenicity, meaning that they cause no signs or only minor clinical signs of infection in poultry.

In influenza seed virus production by reverse genetics, tissue cultures cells are transfected with cDNA clones from the apathogenic high growth A/PuertoRico/8/34 (PR8) backbone and the donor antigenic proteins.

The inventors have prepared recombinant influenza viruses expressing a modified hemagglutinin (HA) from A/Turkey/Indiana/2022. The modified HA comprises changes at its cleavage site that allow the rescued virus to have a phenotype of a low pathogenic HA. The recombinant influenza viruses disclosed express either the neuraminidase (NA) from PR8 (N1), the NA from A/turkey/Indiana/2022 (N1), or the NA from A/BlueWingedTeal/WY/AH0099021/2016 (N9). All three viruses have been confirmed by sequencing to have a low pathogenic cleavage site, the correct NA, and all grow at high enough titers to be a viable vaccine candidate. All these vaccine variants are for use as an inactivated and adjuvanted vaccine.

Just like with human influenza vaccines, having a close match of the influenza strains in the vaccine to the circulating virus is necessary for optimal protection. Multiple RG vaccines to H5 influenza have been produced in the last 20 years, but there are currently no commercial vaccines available that are closely matched to the HPAI virus that is currently circulating in the United States. The advantage to these proposed vaccines is that the vaccine will be closely matched to the field strain which will provide better protection compared to mismatched vaccines. Matching the hemagglutinin protein is critical for protection Matching the neuraminidase protein may provide some additional protection.

The inventors have prepared several vaccine viruses that included an attenuated hemagglutinin protein that is a homologous match to the circulating field strain of the 2022 North American H5N1 highly pathogenic avian influenza virus outbreak which is in the antigenic clade 2.3.4.4b virus. This provides for improved protection as compared to non-clade 2.3.4.4b vaccines, including vaccines targeted to antigenic clades 2.3.4.4a, 2.3.4.4c, 2.2, 2.3.2.1, and related H5 vaccine viruses.

The consideration for using a heterologous neuraminidase protein is for DIVA purposes. DIVA is an acronym for differentiating vaccinated from infected animals, although for trade purposes it typically is understood to differentiate vaccinated-nonexposed poultry from vaccinated and infected poultry. Currently vaccinating for avian influenza has severe trade implications, as countries will not import poultry or poultry products from countries that vaccinate for avian influenza. If a convenient serologic test can reliably identify vaccinated and infected animals, it is possible that the negative trade implications for avian influenza can be overcome. The use of a vaccine with a N9 neuraminidase protein allows for serologic monitoring for the field virus N1 neuraminidase protein. Previous work has shown only a slight loss of protection when using the heterologous neuraminidase protein.

Construction of the three viruses reported herein employs one unique feature not previously reported. All influenza gene segments have a coding region for the protein that is flanked on both ends by non-coding sequence. The non-coding sequence is known to be important in regulating gene expression and packaging of the gene into the virus particle. The noncoding region (NCR) has small regions of highly conserved sequence, but also has regions of variability. As part of the construction of the plasmids for RG rescue, different non-coding regions were used for the N9 neuraminidase gene. This included the sequence found in the original virus, and the same coding sequence with the non-coding region from the PR8 virus. The inventors hypothesized that a virus would replicate better if it had a PR8 non-coding region compatible with the rest of the virus. This change resulted in almost a two-log increase in titer from the native NCR to the PR8 NCR. This effectively makes a virus that did not grow well enough to be used commercially as a vaccine seed strain to a virus that makes an excellent seed strain. The use of PR8 NCR has not been previously identified as being an important factor in virus titer.

Preparation of the vaccine viruses included chimeric constructs of an attenuated HA coding sequence from the circulating field strain and the non-coding sequence from the PR8 virus, or the NA coding sequence from the circulating field strain and the non-coding sequence from the PR8 virus. The use of the chimeric construct provided for improved expression of the hemagglutinin and neuraminidase proteins resulting in higher titers of rescued virus. The improved growth in embryonating chicken eggs allowed for a more economical production of vaccine, which will lower vaccine production costs.

The DIVA principle has also been discussed for many years, but it has not been routinely used for avian influenza, in part because of the lack of convenient companion diagnostic test. Published studies support the heterologous NA DIVA strategy as being a viable option (Avellaneda, G., et al., 2010, "A Heterologous Neuraminidase Subtype Strategy for the Differentiation of Vaccinated and Infected Animals (DIVA) Strategy for Avian Influenza Virus using a more flexible Neuraminidase Inhibition Test," Avian Diseases: 54: 278-286; Jadhao, S J., et al., 2009, "Comparative efficacy of North American and antigenically matched reverse genetics derived H5N9 DIVA marker vaccines against highly pathogenic Asian H5N1 avian influenza in chickens," Vaccine: 27: 6247-6260). Vaccine viruses were prepared that included a neuraminidase gene that is heterologous to the field strain.

Including a neuraminidase gene with a different subtype than the field virus provides for the ability to differentiate vaccinated and non-infected birds from vaccinated and subsequently infected birds by a serologic test. The use of a convenient cost-effective companion diagnostic is required for serologic surveillance to be completed.

In an embodiment, the disclosure relates to a chimeric polynucleotide comprising an hemagglutinin (HA) non-coding sequence from an apathogenic high growth influenza virus and a polynucleotide encoding an attenuated HA protein from a highly pathogenic avian influenza virus or a variant thereof, or a chimeric polynucleotide comprising a neuraminidase (NA) non-coding sequence from an apathogenic high growth influenza virus and a polynucleotide encoding an NA protein from a highly pathogenic avian influenza virus or a variant thereof. In some embodiments of the disclosure the non-coding region in the chimeric poly-nucleotide is from A/PuertoRico/8/34 (PR8). In some embodiments of the disclosure, the HA protein or variant thereof encoded by the chimeric polynucleotide of the disclosure is derived from a highly pathogenic avian influenza virus. In some embodiments of the disclosure, the NA protein or variant thereof encoded by the chimeric poly-nucleotide of the disclosure is derived from a highly pathogenic avian influenza virus. In some embodiments of the disclosure, the HA protein or variant thereof encoded by the chimeric polynucleotide is mutated to comprise an attenu-ated cleavage site. In some embodiments of the disclosure, the HA protein or variant thereof is from A/turkey/Indiana/22-003707-003/2022. In some embodiments of the disclo-sure, the NA protein or variant thereof encoded by the chimeric polynucleotide is an N1, N2, N3, N4, N5, N6, N7, N8, or N9. In some embodiments of the disclosure, the NA protein or variant thereof encoded by the chimeric poly-nucleotide is from A/turkey/Indiana/22-003707-003/2022. In some embodiments of the disclosure, the NA protein or variant thereof encoded by the chimeric polynucleotide is from A/Blue Winged Teal/Wyoming/AH0099021/2016.

In some embodiments, the disclosure relates to a poly-nucleotide encoding a variant attenuated HA protein from A/turkey/Indiana/22-003707-003/2022. The hemagglutinin or haemagglutinin (HA) glycoprotein of influenza virus is a homotrimeric integral membrane protein found on the sur-face of influenza viruses. The HA protein has multifunc-tional activity as an attachment factor and as a membrane fusion protein. A polynucleotide encoding an HA protein variant may have less than 100% identity to the polynucle-otide encoding an attenuated A/turkey/Indiana/22-003707-003/2022 HA protein, but may retain the multifunctional activity of the HA protein. For example, the attenuated HA protein may be encoded by a polynucleotide having at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to the nucleotide sequence set forth in SEQ ID NO:3 while retaining its multifunctional activity as an attachment factor and a membrane fusion protein.

In some embodiments, the disclosure relates to a poly-nucleotide encoding an NA protein from a highly pathogenic avian influenza virus or a variant thereof. The influenza neuraminidase (NA) is found on the virion surface and plays an essential role in release and spread of progeny virions from infected cells. A polynucleotide encoding an NA protein variant may have less than 100% identity to the polynucleotide encoding a A/turkey/Indiana/22-003707-003/2022 NA protein or a A/Blue Winged Teal/Wyoming/AH0099021/2016 NA protein while still retaining its viral release and spread activities. For example, the NA protein may be encoded by a polynucleotide having at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to the nucleotide sequence set forth in SEQ ID NO:4 or SEQ ID NO: 5 while retaining its viral release and spread activities.

In an embodiment, the disclosure relates to a rescued influenza virus comprising polynucleotides encoding influ-enza A M1/M2, NP, PB1, PA, PB2, and NS1/NS2 from an apathogenic high growth influenza virus, a polynucleotide encoding an HA from A/turkey/Indiana/22-003707-003/2022 modified to comprise a low pathogenic cleavage site, and a polynucleotide encoding an N1, N2, N3, N4, N5, N6, N7, N8, or N9 NA. In some embodiments of the disclosure, the polynucleotide encoding NA in the rescued influenza virus is from A/turkey/Indiana/22-003707-003/2022 or A/Blue Winged Teal/Wyoming/AH0099021/2016. In some embodiments of the disclosure the rescued influenza virus polynucleotides encoding influenza A M1/M2, NP, PB1, PA, PB2, and NS1/NS2 are from PR8.

In an embodiment, the disclosure relates to a vector comprising a chimeric polynucleotide of the disclosure. In some embodiments of the disclosure, the vector is a plasmid, a cosmid, a phage, a virus, or a fragment of a virus. In an embodiment, the disclosure relates to a rescued influenza virus comprising polynucleotides encoding influenza A M1/M2, NP, PB1, PA, PB2, and NS1/NS2 from an apatho-genic high growth influenza virus, a polynucleotide encod-ing an HA from A/turkey/Indiana/22-003707-003/2022 modified to comprise a low pathogenic cleavage site, and a polynucleotide encoding an N1, N2, N3, N4, N5, N6, N7, N8, or N9 NA. In some embodiments of the disclosure, the polynucleotide encoding NA in the rescued influenza virus is from A/turkey/Indiana/22-003707-003/2022 or A/Blue Winged Teal/Wyoming/AH0099021/2016. In some embodi-ments of the disclosure the polynucleotides encoding influ-enza A M1/M2, NP, PB1, PA, PB2, and NS1/NS2 in the rescued influenza virus are from PR8. In an embodiment, the disclosure relates to an immunogenic composition compris-ing an immunologically-effective amount of the rescued influenza virus of the disclosure.

In an embodiment, the disclosure relates to a method of producing an influenza virus, the method comprising intro-ducing into a population of host cells a plurality of vectors comprising polynucleotides corresponding to at least six internal segments of an apathogenic high growth influenza virus, a chimeric polynucleotide comprising a non-coding sequence from an apathogenic high growth influenza virus and a polynucleotide encoding an HA protein from a highly pathogenic avian influenza virus or variant thereof, and a chimeric polynucleotide comprising a non-coding sequence from an apathogenic high growth influenza virus and a polynucleotide encoding an NA protein from a highly patho-genic avian influenza virus or variant thereof, culturing the population of host cells at a temperature that is less or equal to 35° C., and recovering the virus. In some embodiments of the disclosure, the influenza virus is produced with PR8 as the apathogenic virus, an HA or variant thereof from A/tur-key/Indiana/22-003707-003/2022, and the NA is N1, N2, N3, N4, N5, N6, N7, N8, or N9.

In an embodiment, the disclosure relates to a method of producing an influenza virus, the method comprising intro-ducing into a population of host cells a plurality of vectors comprising polynucleotides corresponding to at least six internal segments of an apathogenic high growth influenza virus, a polynucleotide encoding A/turkey/Indiana/22-003707-003/2022 HA or a variant thereof, and an NA polynucleotide of N1, N2, N3, N4, N5, N6, N7, N8, or N9, culturing the population of host cells at a temperature that is less or equal to 35° C., and recovering the virus. In some embodiments of the disclosure the apathogenic virus in the method of producing an influenza virus is PR8. In some embodiments of the disclosure, the NA polynucleotide in the method of producing an influenza virus is from A/turkey/Indiana/22-003707-003/2022 or A/Blue Winged Teal/Wyoming/AH0099021/2016.

Embodiments of the present disclosure are shown and described herein. It will be obvious to those skilled in the art that such embodiments are provided by way of example only. Numerous variations, changes, and substitutions will occur to those skilled in the art without departing from the disclosure. Various alternatives to the embodiments of the disclosure described herein may be employed in practicing the disclosure. It is intended that the included claims define the scope of the disclosure and that methods and structures within the scope of these claims and their equivalents are covered thereby. All publications, patents, and patent applications mentioned in this specification are herein incorporated by reference to the same extent as if each individual publication, patent, or patent application was specifically and individually indicated to be incorporated by reference.

EXAMPLES

Having now generally described this disclosure, the same will be better understood by reference to certain specific examples, which are included herein only to further illustrate the disclosure and are not intended to limit the scope of the disclosure as defined by the claims.

Example 1

Preparation of Viruses and Vaccines

Using reverse genetics, viruses comprising polynucleotides encoding the A/turkey/Indiana/22-003707-003/2022 virus HA and/or NA, or the NA from the PR8 virus, from an N3 virus, from an N4 virus, or from an N9 virus were assembled.

The coding sequence from the A/turkey/Indiana/22-003707-003/2022 (TK/IN/22) virus was obtained from GISAID (Global Initiative on Sharing All Influenza Data). The hemagglutinin (HA) gene sequence was altered to change the highly pathogenic cleavage site to a low pathogenic cleavage site. The HA coding sequence was modified to change the cleavage site from REKRRKR/GLF (set forth in SEQ ID NO: 1) to RETR/GLF (set forth in SEQ ID NO: 2) which included the deletion of three basic amino acids, and substitution of Threonine for Lysine at the −2 position from cleavage site. The gene sequence was additionally modified to include the non-coding gene sequence that was not included in the publicly available sequence. This sequence was de novo synthesized by IDT DNA to include the non-coding and coding sequence with additional non-influenza sequence (DNA assembly sites) to facilitate insertion of the sequence into the plasmid. The N1 neuraminidase sequence gene from the A/turkey/Indiana/22-003707-003/2022 was also de novo synthesized with the coding, non-coding, and non-influenza sequences. The N9 neuraminidase gene from A/Blue Winged Teal/Wyoming/AH0099021/2016 was also de novo synthesized with the coding, noncoding, and non-influenza sequences. The sequence of the A/turkey/Indiana/22-003707-003/2022 HA is set forth in SEQ ID NO: 3; the sequence of the A/turkey/Indiana/22-003707-003/2022 NA is set forth in SEQ ID NO: 4; the sequence of the A/Blue Winged Teal/Wyoming/AH0099021/2016 NA is set forth in SEQ ID NO: 5.

Using DNA assembly enzyme, the sequences for each individual gene were inserted into a plasmid that includes an RNA polymerase promoter and a transcription promoter. The HA and NA influenza-encoding fragments were inserted between the PR8 HA and NA non-coding regions, and the internal PR8 genes were as normally found. Using this reverse genetics plasmid, the viral RNA is transcribed as well as mRNA that expresses the viral proteins necessary for viral packaging. In addition to the hemagglutinin (HA) gene, a neuraminidase (NA) gene, and the 6 other viral gene segments are necessary for rescue. The 6 internal genes are derived from the PR8 vaccine virus. The neuraminidase gene was obtained from either A/turkey/Indiana/22-003707-003/2022, the PR8 virus, or an N3, an N4, or an N9 influenza virus.

The plasmids carrying the HA-encoding sequences and the neuraminidase (NA) gene plasmid were introduced with polynucleotides encoding the other 6 required genes from PR8 vaccine strain, PB2, PB1, PA, NP, M1/M2, and NS, and were transfected into cell culture to rescue a live vaccine virus. A total of 8 genes are necessary to rescue a virus.

The eight gene segments were transfected into 293T cells using TransIT-LT1 Transfection reagent, a commercial product. After 2 days the cell supernatant was inoculated into embryonating chicken eggs. And after 5 days the allantoic fluid was tested for hemagglutinating activity, which is evidence of a rescued virus.

Rescued viruses were sequenced to ensure the low pathogenic cleavage site was present. To confirm that the rescued viruses were low pathogenic, the viruses were grown in cell culture with and without trypsin. Low pathogenic viruses require trypsin to grow in cell culture media.

Low pathogenic viruses were tittered, and three viruses were selected for further studies. The viruses selected for further studies were A/turkey/Indiana/22-003707-003/2022 (HA-LPAI), PR/8 (N1,MA, NS, PA, PB1, PB2 and NP) 10^9.2 EID50/mL; A/turkey/Indiana/22-003707-003/2022 (HA-LPAI and N1), PR/8 (MA, NS, PA, PB1, PB2 and NP) 10^9.4 EID50/mL. With the original non-coding region, A/turkey/Indiana/22-003707-003/2022 (HA-LPAI), A/Blue Winged Teal/Wyoming/AH0099021/2016 (N9), PR/8 (MA, NS, PA, PB1, PB2 and NP) presented with 10^7.6 EID50/mL. With the PR8 on-coding region, A/turkey/Indiana/22-003707-003/2022 (HA-LPAI), A/Blue Winged Teal/Wyoming/AH0099021/2016 (N9), PR/8 (MA, NS, PA, PB1, PB2 and NP) presented with 10^9.5 EID50/mL Two candidate viruses were selected, an H5N1 virus comprising polynucleotides encoding A/turkey/Indiana/22-003707-003/2022 NA and attenuated HA, and an H5N9 virus comprising polynucleotides encoding the A/turkey/Indiana/22-003707-003/2022 attenuated HA and the A/Blue Winged Teal/Wyoming/AH0099021/2016 NA (N9).

This Example shows the rescue of candidate viruses comprising an attenuated A/turkey/Indiana/22-003707-003/2022 HA and NA, and a candidate viruses comprising the attenuated A/turkey/Indiana/22-003707-003/2022 HA and the A/Blue Winged Teal/Wyoming/AH0099021/2016 NA with the PR3 non-coding regions or the A/Blue Winged Teal/Wyoming/AH0099021/2016 non-coding regions.

We claim:

1. A chimeric polynucleotide comprising:

(i) a hemagglutinin (HA) non-coding sequence from an A/Puerto Rico/8/34 (PR8) apathogenic high growth influenza virus and a polynucleotide encoding an attenuated HA protein from an A/turkey/Indian/22-003707-003/2022 highly pathogenic avian influenza virus or a variant thereof having at least 96% identity thereto, wherein the wild type A/turkey/Indian/22-003707-003/2022 HA nucleotide sequence is set forth in SEQ ID NO: 3; or (ii) a neuraminidase (NA) non-coding sequence from an PR8 apathogenic high growth influenza virus and a polynucleotide encoding an NA protein from an A/turkey/Indian/22-003707-003/2022 highly pathogenic avian influenza virus or a variant thereof having at least 96% identity thereto, wherein the wild type A/turkey/Indian/22-003707-003/2022 NA nucleotide sequence is set forth in SEQ ID NO: 3; or (iii) an NA non-coding sequence from an PR8 apathogenic high growth influenza virus and a polynucleotide encoding an NA protein from a A/Blue Winged Teal/Wyoming/AH0099021/2016 low pathogenic influenza virus or a variant thereof having at least 96% identity thereto, wherein the wild type A/Blue Winged Teal/Wyoming/AH0099021/2016 NA nucleotide sequence is set forth in SEQ ID NO: 3;

wherein the HA is attenuated by altering the highly pathogenic cleavage site into a low pathogenic cleavage site.

2. A vector comprising a chimeric polynucleotide of claim 1.

3. The vector of claim 2, wherein the vector is a plasmid, a cosmid, a phage, a virus, or a fragment of a virus.

4. A cell comprising the vector of claim 2.

5. A rescued influenza virus comprising polynucleotides encoding M1/M2, NP, PB1, PA, PB2, and NS1/NS2 from an PR8 apathogenic high growth influenza A virus, a polynucleotide encoding an attenuated HA from a A/turkey/Indiana/22-003707-003/2022 high highly pathogenic avian influenza virus or a variant thereof having 96% identity thereto, and a polynucleotide encoding an N1, N2, N3, N4, N5, N6, N7, N8, or N9 NA; wherein the wild type A/turkey/Indian/22-003707-003/2022 HA nucleotide sequence is set forth in SEQ ID NO: 3;

wherein the HA is attenuated by altering the highly pathogenic cleavage site into a low pathogenic cleavage site.

6. The rescued influenza virus from claim 5, wherein the polynucleotide encoding NA is from A/turkey/Indiana/22-003707-003/2022 having the nucleotide sequence of SEQ ID NO: 4, A/Blue Winged Teal/Wyoming/AH0099021/2016 having the nucleotide sequence of SEQ ID NO: 5, or a variant thereof having 96% identity thereto.

7. The rescued influenza virus of claim 6, wherein the polynucleotide encoding NA is from A/turkey/Indiana/22-003707-003/2022 having the nucleotide sequence of SEQ ID NO: 4.

8. The rescued influenza virus of claim 6, wherein the polynucleotide encoding NA is from A/Blue Winged Teal/Wyoming/AH0099021/2016 having the nucleotide sequence of SEQ ID NO: 5.

9. An expression vector comprising any one of the polynucleotides encoding M1/M2, NP, PB1, PA, PB2, NS1/NS2, HA, or NA of claim 5.

10. An immunogenic composition comprising an immunologically-effective amount of the rescued influenza virus of claim 5.

11. A method of producing an influenza virus, the method comprising introducing into a population of host cells a plurality of vectors comprising polynucleotides corresponding to at least six internal segments of an PR8 apathogenic high growth influenza virus, a chimeric polynucleotide comprising an HA non-coding sequence from an PR8 apathogenic high growth influenza virus and a polynucleotide encoding an attenuated HA protein from a A/turkey/Indiana/22-003707-003/2022 highly pathogenic avian influenza virus or a variant thereof having 96% identity thereto, and a chimeric polynucleotide comprising an NA non-coding sequence from an PR8 apathogenic high growth influenza virus and a polynucleotide encoding an N1, N2, N3, N4, N5, N6, N7, N8, or N9 NA protein or a variant thereof having 96% identity thereto, culturing the population of host cells at a temperature that is less or equal to about 35° C., and recovering the virus;

wherein the wild type A/turkey/Indian/22-003707-003/2022 HA nucleotide sequence is set forth in SEQ ID NO: 3; and wherein the HA is attenuated by altering the highly pathogenic cleavage site into a low pathogenic cleavage site.

12. The method of claim 11, wherein the NA is from A/turkey/Indiana/22-003707-003/2022 having the nucleotide sequence of SEQ ID NO: 4, A/Blue Winged Teal/Wyoming/AH0099021/2016 having the nucleotide sequence of SEQ ID NO: 5, or a variant thereof having 96% identity thereto.

13. The method of claim 12, wherein the NA polynucleotide is from A/turkey/Indiana/22-003707-003/2022 having the nucleotide sequence of SEQ ID NO: 4, or A/Blue Winged Teal/Wyoming/AH0099021/2016 having the nucleotide sequence of SEQ ID NO: 5.

* * * * *

SEQUENCE LISTING

Sequence total quantity: 5
SEQ ID NO: 1              moltype = AA   length = 10
FEATURE                   Location/Qualifiers
source                    1..10
                          mol_type = protein
                          organism = synthetic construct
SEQUENCE: 1
REKRRKRGLF                                                          10

SEQ ID NO: 2              moltype = AA   length = 7
FEATURE                   Location/Qualifiers
source                    1..7
                          mol_type = protein
                          organism = synthetic construct
SEQUENCE: 2
RETRGLF                                                             7

SEQ ID NO: 3              moltype = DNA   length = 1772
FEATURE                   Location/Qualifiers
source                    1..1772
                          mol_type = other DNA
                          organism = synthetic construct
SEQUENCE: 3
agcaaaagca gggggaaaata aaaacaacca aaatggagaa catagtacta cttcttgcaa   60
tagttagcct tgttaaaagt gatcagattt gcattggtta ccatgcaaac aattcgacag   120
agcaagttga cacgataatg gaaaagaacg tcactgttac acatgcccaa gacatactgg   180
aaaaaacaca caacgggaag ctctgtgatc taaatggggt gaagcctctg attttaaagg   240
attgtagtgt agctggatgg ctcctcggaa acccaatgtg cgacgaattc atcagagtgc   300
cggaatggtc ctacatagtg gagcgggcta acccagctaa tgacctctgt tacccaggga   360
gcctcaatga ctatgaagaa ctgaaacaca tgttgagcag aataaatcat tttgagaaga   420
ttctgatcat tcccaagagt tcctggccaa atcatgaaac atcactaggg gtgagcgcag   480
cttgtccata ccagggagcg ccctcctttt tcagaaatgt ggtgtggctt atcaaaaaga   540
acgatgcata cccaacaata aagataagct acaataatac caatcgggaa gatctcttga   600
tactgtgggg gattcatcat tccaacaatg cagaagagca gacaaatctc tacaaaaacc   660
caaccaccta catttcagtt ggaacatcaa ctttaaacca gaggttggca ccaaaaatag   720
ctactagatc ccaagtaaac gggcaacgtg gaagaatgga cttcttctgg acaatcttaa   780
aaccagatga tgcaatccat ttcgagagta atggaaattt cattgctcca gaatatgcat   840
acaaaattgt caagaaaggg gactcaacaa ttatgaaaag tggagtggaa tatggccact   900
gcaacaccaa atgtcaaacc ccagtaggtg cgataaattc tagtatgcca ttccacaaca   960
tacatcctct caccattggg gaatgcccca aatacgtgaa gtcaaacaag ttggtccttg   1020
cgactgggct cagaaatagt cctctaagag aaactagagg cctgtttggg gcgatagcag   1080
ggtttataga gggaggatgg cagggaatgg ttgatggttg gtatgggtac catcatagca   1140
atgagcaggg gagtgggtat gctgcggaca agaatccac ccaaaaggca atagatggag   1200
ttaccaataa ggtcaactca atcattgaca aaatgaacac tcaatttgac gcagttggaa   1260
gggagtttaa taacttagaa aggaggatag agaatttgaa caagaaaatg gaagacggat   1320
tcctagatgt ctggacctat aatgctgaac ttctagttct catggaaaac gagaggactc   1380
tagatttcca tgattcaaat gtcaagaacc tttacgacaa agtcagatta cagcttaggg   1440
ataatgcaaa ggagctgggt aacggctgtt tcgaattcta tcacaaatgt gataatgaat   1500
gtatggaaag tgtgagaaat gggacgtatg actaccctca gtattcagaa gaagcaagat   1560
taaaaagaga agaaataagc ggagtgaaat tagaatcagt aggaacttac cagatactgt   1620
caatttattc aacagcggca agttccctag cactggcaat catgatggct ggtctatctt   1680
tatggatgtg ctccaatggg tcgttacagt gcagaatttg catttaggat tagaatttca   1740
gaaatatgag gaaaaacacc cttgtttcta ct                                1772

SEQ ID NO: 4              moltype = DNA   length = 1458
FEATURE                   Location/Qualifiers
source                    1..1458
                          mol_type = other DNA
                          organism = synthetic construct
SEQUENCE: 4
agcaaaagca ggagtttaaa atgaatccaa atcaaaagat aacaaccatt ggatcaatct   60
gtatggtaat tgggatagtc agcttgatgc tgcaaattgg gaacataatc tcaatatggg   120
ttagccattc aatccaaaca gggaatcaat accagcctga accatgcaat caaagcatca   180
ttacctatga gaacaacacc tgggtaaatc agacgtatgt caacatcagc aataccaatt   240
ttcttgctga gcaggctgtt acttcggtaa cattagcggg caattcatct ctttgcccta   300
ttagtgggtg ggcaatatac agtaaggaca acggtataag aattgggtcc aaggggatg   360
tgtttgtcat aagagaaccg ttcatctcat gctccacttt ggaatgcaga accttttccc   420
tgacccaggg agctctgctg aatgacaaac attctaatgg accgttaag gatagaagcc   480
cttatagaac tttgatgagt gtcccgtgg gtgaggctcc ttccccgtac aattcaagat   540
ttgagtctgt tgcttggtcg gcaagtgctt gtcatgatgg catcagttgg ttgacaatcg   600
gtatttctgg tccagacaat ggagctgtgg ctgtattgaa gtacaatggc ataatcacgg   660
atactatcaa gagttggaga aacaacattt tgagaactca gaatctgaa tgtgcgtgcg   720
taaatggctc ttgcttcact taatgactg atggaccaag caatgggcag gcctcatata   780
aaatcttcaa gatagagaaa gggaaagttg tcaaatcagt tgaattgaat gcccctaatt   840
accactacga ggaatgctcc tgttatcctg atgcgggtga tattatgtgt gtgtgcaggg   900
acaattggca tggctcaaac cggccgtggg tatcttttaa tcaaaatctg gagtatcaaa   960
taggatatat atgcagtggg gttttcgggg acaatcccg ccccaatgat ggaacaggca   1020
gttgcagtcc aatgtcctct aatgggcat atggggtaaa agggttttca tttaagtacg   1080

-continued

```
gtaatggggt ttggatcgga agaacaaaaa gcactagttc cagaagcggc tttgagatga  1140
tttgggatcc gaatgggtgg actgagacgg acagtagttt ctcagtgaag caagacattg  1200
tagaaataac tgactggtca ggatatagtg ggagttttgt ccagcatcca gaactgacag  1260
ggttagattg catgaggcct tgtttctggg ttgagctaat tagagggagg cccaaagaga  1320
acacaatttg gactagcggg agcagcatat ccttttgtgg tgtaaatagt gacactgtgg  1380
gttggtcttg gccagacggt gctgagttgc cattcaccat tgacaagtag tctgttcaaa  1440
aaactccttg tttctact                                                1458

SEQ ID NO: 5                moltype = DNA  length = 1461
FEATURE                     Location/Qualifiers
source                      1..1461
                            mol_type = other DNA
                            organism = synthetic construct
SEQUENCE: 5
agcaaaagca ggagtttaaa atgaatccaa atcagaagat tctatgcact tctgccactg   60
ctattgtaat aggcacgatt gcagtactca taggaatagc aaacctggga ctgaacatag  120
gactacatct gaaaccaaac tgcaactgct caaactcaca atctgaaaca agcaatgcaa  180
gccaaacaat aataaacaac tactataacg aaacaaacat cactcaaata agcaacacca  240
acatccaaat ggaggagaaa gcaaatagag aattcaacaa cttgaccaaa ggactctgca  300
ctataaattc atggcacatc tacgggaaag acaatgcagt aagaattggg gagaactcag  360
atgttctagt aacgagagag ccctatgtct cctgtgatcc aaatgagtgc aggttctatg  420
ctctcagcca aggaacaacg attagaggga aacactcaaa tggaacaata cagcatagat  480
cccagtaccg cgccctgata agctggccac tgtcatcacc acccacagta tacaacagca  540
ggatagaatg cattggttgg tcaagtacta gctgtcatga tggtagagcc aggatgtcaa  600
tatgtatatc aggcccgaac aacaatgcgt cagctgtaat ttggtacaat agaagacctg  660
ttacagaaat caatacatgg gcccgaaaca tactacggac acaagaatct gaatgcgtat  720
gccacaacgg tatctgcccg gtagtattca cagatgggtc tgccactgga cctgcagaaa  780
caagagtata ctatttcaaa gaagggaaaa tactaaaatg ggaacctcta actgggactg  840
ctaaacacat tgaagaatgc tcatgctatg gggtgcaagc aggtattact tgcacgtgca  900
gggataattg gcagggttcg aatagaccag taattcaaat agatccagtg gcaatgacac  960
acactagtca gtatatatgt agccctgttc ttacagataa tccccggccg aacgacccag  1020
cagtaggtaa gtgcaatgac ccctacccag gaaacaacaa caatggagtc aaagggtttt  1080
catcctgga tggaggtaat acttggctag gaagaacaat aagcacagct tccagatcag  1140
gatatgagat gctaaaggta ccaaatgcat tgaccgacga taggtcaaaa cccactcaag  1200
gccaaacaat tgtattaaac actgactgga gtggctacag tggatccttc atggactatt  1260
gggctgaagg ggaatgctac cgagcgtgtt tttacgtgga gttaatacgc ggaaggccca  1320
aggaggacaa agtatggtgg accagtaata gtatagtatc aatgtgttcc agcacagaat  1380
tccttggaca atggaactgg cctgatgggg ctaaaataga gtacttcctc taatctgttc  1440
aaaaaactcc ttgtttctac t                                            1461
```